(12) United States Patent
Kim (10) Patent No.: US 9,949,736 B2
(45) Date of Patent: Apr. 24, 2018

(54) APPARATUS FOR FORMING COGS ON SURGICAL THREAD AND METHOD THEREFOR

(71) Applicant: Chun Dong Kim, Suwon-si (KR)

(72) Inventor: Chun Dong Kim, Suwon-si (KR)

( * ) Notice: Subject to any disclaimer, the term of this patent is extended or adjusted under 35 U.S.C. 154(b) by 171 days.

(21) Appl. No.: 15/034,180

(22) PCT Filed: Nov. 6, 2014

(86) PCT No.: PCT/KR2014/010626
§ 371 (c)(1),
(2) Date: May 4, 2016

(87) PCT Pub. No.: WO2015/069042
PCT Pub. Date: May 14, 2015

(65) Prior Publication Data
US 2016/0278769 A1    Sep. 29, 2016

(30) Foreign Application Priority Data

Nov. 7, 2013  (KR) .................. 10-2013-0134638

(51) Int. Cl.
| | | |
|---|---|---|
| *D02J 3/02* | (2006.01) | |
| *A61B 17/06* | (2006.01) | |
| *D02J 3/10* | (2006.01) | |
| *B26D 1/45* | (2006.01) | |
| *A61B 17/04* | (2006.01) | |
| *B26D 5/00* | (2006.01) | |
| *B26D 7/14* | (2006.01) | |
| *A61B 17/00* | (2006.01) | |

(52) U.S. Cl.
CPC ........ *A61B 17/06166* (2013.01); *A61B 17/04* (2013.01); *B26D 1/455* (2013.01);
(Continued)

(58) Field of Classification Search
CPC ...... D02J 3/02; D02J 3/10; D02J 1/06; D02G 1/10; A61B 2017/06176; A61B 17/06166;
(Continued)

(56) References Cited

U.S. PATENT DOCUMENTS

| | | | | |
|---|---|---|---|---|
| 3,620,114 A | * | 11/1971 | Chudyk | ................... D06H 7/00 83/107 |
| 3,648,485 A | * | 3/1972 | Boy | ....................... D04B 15/60 66/134 |

(Continued)

FOREIGN PATENT DOCUMENTS

| | | |
|---|---|---|
| JP | 07-278997 A | 10/1995 |
| JP | 2010-259786 A | 11/2010 |

(Continued)

OTHER PUBLICATIONS

International Search Report for PCT/KR2014/010626 dated Dec. 19, 2014 from Korean Intellectual Property Office.

*Primary Examiner* — Amy Vanatta
(74) *Attorney, Agent, or Firm* — Revolution IP, PLLC (57) ABSTRACT

Disclosed is an an apparatus for forming cogs on a surgical thread, comprising: a bobbin having a suture thread wound thereonto; first and second tension rolls for maintaining, at regular tensions, the suture thread unwound from the bobbin; a pair of friction rolls for drawing the suture thread and allowing the suture thread to pass through so as to be discharged through an outgoing side; a tension plate operating up and down, for temporarily fixing the suture thread being discharged through the outgoing side by the friction roll; and a cog-forming knife for forming cogs by rotating and simultaneously moving forward toward the suture thread fixed by the tension plate and also obliquely moving to the left or the right so as to make oblique cuts on the surface of the suture thread.

13 Claims, 8 Drawing Sheets

(52) U.S. Cl.
CPC ............... *B26D 5/005* (2013.01); *B26D 7/14* (2013.01); *D02J 3/02* (2013.01); *D02J 3/10* (2013.01); *A61B 2017/00526* (2013.01); *A61B 2017/06176* (2013.01)

(58) Field of Classification Search
CPC ..................... A61B 17/04; A61B 2017/00526; B26D 3/08; B26D 1/455; B26D 1/1575; B26D 1/18; B26D 1/185; B26D 1/28; B26D 1/285; B26D 7/01; B26D 3/12; B26D 7/14; B26D 5/005
See application file for complete search history.

(56) References Cited

U.S. PATENT DOCUMENTS

| | | | |
|---|---|---|---|
| 7,996,967 B2* | 8/2011 | Genova | A61B 17/06166 29/7.1 |
| 2002/0033429 A1* | 3/2002 | Jaschke | B65H 54/34 242/481.4 |
| 2003/0041426 A1* | 3/2003 | Genova | A61B 17/06166 29/7.1 |
| 2004/0226427 A1* | 11/2004 | Trull | A61B 17/06166 83/651 |
| 2005/0234480 A1* | 10/2005 | Nam | A61B 17/06166 606/148 |
| 2009/0076543 A1* | 3/2009 | Maiorino | A61B 17/06166 606/228 |
| 2010/0275750 A1* | 11/2010 | Maiorino | A61B 17/06166 83/13 |
| 2011/0106152 A1* | 5/2011 | Kozlowski | A61B 17/06166 606/228 |
| 2013/0238021 A1* | 9/2013 | Gross | A61B 17/06166 606/228 |

FOREIGN PATENT DOCUMENTS

| | | |
|---|---|---|
| KR | 10-0465670 B1 | 1/2005 |
| KR | 10-2008-0096980 A | 11/2008 |

* cited by examiner

APPARATUS FOR FORMING COGS ON SURGICAL THREAD AND METHOD THEREFOR

CROSS REFERENCE TO PRIOR APPLICATIONS

This application is a National Stage Application of PCT International Patent Application No. PCT/KR2014/010626 filed on Nov. 6, 2014, under 35 U.S.C. § 371, which claims priority to Korean Patent Application No. 10-2013-0134638 filed on Nov. 7, 2013, which are all hereby incorporated by reference in their entirety.

TECHNICAL FIELD

The present invention relates to an apparatus for forming cogs on a surgical thread and a method thereof, and more particularly, to an apparatus for forming cogs on a surgical thread which automatically forms cogs with a desired pattern on an external surface of a surgical thread to improve productivity and quality, and a method thereof.

BACKGROUND ART

Generally, when an incision is sutured after a surgical operation, the incision is stitched and tied using a medical thread (monofilament suture) and finished by forming a knot to prevent skin from opening.

Accordingly, when a surgical area or wound area is sutured or fixed, there are disadvantages of requiring a long time to tie a thread several times and, especially, distinct scars being left by the thread and knot at the sutured area.

To improve this, in the registered utility No. 0320005, a medical thread was disclosed in which cogs in a hook shape are formed to be inclined in one direction, in both directions in which the cogs face each other, or in a zigzag direction, or are formed in a saw tooth shape on a surface of the thread for suturing which has good tensile strength such as nylon or prolene such that when the thread is inserted under skin, the fixing characteristic is maintained even without tying the inserted thread due to a cog structure.

A medical thread having such cogs may have various shapes illustrated in FIGS. 1A, 1B, 1C, and 1D may be used for medical practices such as suturing a split wound during an operation, pulling up muscles, forming collagen, pulling up organs, or the like, and provide a help to simplify a complex suture and decrease operation time because the thread does not slide or is not pulled out and maintains a pulling force even when the thread is pulled in a direction at which cogs protrude.

In addition, the suture may be easily and conveniently completed by only simply cutting the thread which comes out of skin, tissue, or muscles.

Accordingly, since a knot is not needed with a medical thread having such cogs, the medical thread is useful for an endoscopic operation. In addition, when the medical thread is used for suturing after being soaked in a specific medicated liquid, it becomes possible for the medical thread to deliver the medication as the medication remaining between the cogs gradually permeates, and furthermore, since the medical thread may also grip and lift up the substances causing artery hardening, the medical thread may also be applied for removing a blood clot without needing to cut a blood vessel.

However, when such cogs are formed in a suture thread, since the cogs are formed nowadays by manually making cuts on an external surface of the suture thread using a user's knife, productivity is very low, quality is also low, and thus there is a disadvantage in that efficiency is very low.

That is, since the suture thread is very thin, working is cumbersome because a user must work with a magnifying glass to manually cut the suture thread, and thus there is a disadvantage in that productivity is extremely decreased.

DISCLOSURE

Technical Problem

The present invention is directed to providing an apparatus for forming cogs on a surgical thread, using which production efficiency is increased, cost is reduced, and quality is improved due to automatically producing the suture thread having the cogs using a mechanical method, and a method thereof.

Technical Solution

One aspect of the present invention provides an apparatus for forming cogs on a surgical thread, the apparatus including: a bobbin (110) around which a suture thread (100) is wound; first and second tension rolls (200 and 210) which maintain the suture thread (100) unwound from the bobbin (110) at a constant tensile force; a pair of friction rolls (300) through which the suture thread (100) passes to be discharged toward an output side by being pulled; a push lever (330) which temporally fixes the suture thread (100) moved toward the output side by the friction rolls (300) and moves upward and downward; and a cog-forming knife (400) which simultaneously rotates and moves forward toward the suture thread (100) fixed by the push lever (330), obliquely moves to the left or right, and forms a cut in an inclined shape on a surface of the suture thread (100) to form a cog.

Here, roughness may be provided on surfaces of the pair of friction rolls (300).

In addition, any one of the pair of friction rolls (300) may be provided to vertically move to twist and move the suture thread (100).

In addition, a gap between the pair of friction rolls (300) may be widened by a roller opening lever (304) operated by the principle of the lever.

In addition, the cog-forming knife (400) may be fixed to a rotational shaft of a fourth motor (410) so that an angle is adjustable; the fourth motor (410) may be fixed to a motor base (420) in an 'L' shape; a rotating wheel (440) having a diameter greater than a width of the motor base (420) may be fixed on a bent lower end surface thereof; the rotating wheel (440) may be disposed to come into contact with any one of the pair of first and second inclination guides (450a and 450b) which are obliquely arranged so that the rotating wheel (440) is interposed therebetween; the motor base (420) may be provided to be movable in X and Y directions by a plurality of sliders (422 and 426) and linear motors (LM) (424 and 428); and the motor base (420) may be connected to a ball screw (490) rotated by a fifth motor (500) and be provided movably.

Further, leading ends of the first and second inclination guides (450a and 450b) may be linked to each other by a micrometer (460) which is a fine adjustment unit and adjust an inclination and a depth of a cut forming a cog by adjusting an inclination of the first and second inclination guides (450a and 450b).

In addition, a rotating wheel (440) which comes into contact with any one of the first and second inclination guides (450a and 450b) may be adjusted by laterally moving the motor base (420) using a lateral operation bench (600) in a rod shape which is straightly moved in a lateral direction by a sixth motor (610).

Cutting scissors (350) may be further provided at a side of an output side, at which the suture thread (100) is discharged after a cog is formed on the suture thread (100), to cut the suture thread (100) by a predetermined length.

One aspect of the present invention provides a method of forming a cog on a surgical thread using the apparatus for forming cogs on a surgical tread, the method including: preparing for extracting a suture thread (S100) so that the suture thread (100) wound around the bobbin (110) passes between the first and second tension rolls (200) and (210) and the friction rolls (300) and is disposed toward the output side to extract the suture thread (110); setting a direction of cog forming (S110) that determines and sets whether a cog to be formed on the suture thread (100) is formed in a length direction of the suture thread (100) or in a direction opposite the length direction when the suture thread (100) is maintained in an extractable state; starting cog forming (S120) that simultaneously extracts the suture thread (100), moves and rotates a cog-forming knife (400), and moves the cog-forming knife (400) in an inclined direction to form a cut in a predetermined direction on the surface of the suture thread (100) when the setting of the direction of the cog forming is completed; and cutting a suture thread (S130) which cuts the suture thread (100) by a predetermined length using the cutting scissors (350) when a predetermined length or the set number of cogs are formed.

Advantageous Effects

According to the embodiment of the present invention, productivity can be improved and production yield can be increased by automatically forming the cogs, quality can be improved by sequentially forming elaborate cogs using programmatic control, and production cost can be reduced since a mass production is possible.

MODES OF THE INVENTION

Hereinafter, exemplary embodiments of the present invention will be described in detail with reference to accompanying drawings.

In the description of the present invention, since the following specific structures or functional descriptions are exemplified only to describe embodiments according to a concept of the present invention, the embodiments according to the present invention may be made with various forms, and the embodiments described in the specification should not be considered to be limited to the embodiments described in the specification.

Also, while the invention is susceptible to various modifications and alternative forms, specific embodiments thereof are shown by way of examples in the drawings and will herein be described in detail. It should be understood, however, that there is no intent to limit the invention to the particular forms disclosed, and on the contrary, the invention covers all modifications, equivalents, and alternatives falling within the spirit and scope of the invention.

In the embodiment of the present invention, cogs are formed on a surgical thread using a sharp knife for maintaining a desired tensile force by hooking the cogs to a muscle when the surgical thread is inserted into skin.

Here, since the uses of the cogs are different, the cogs are also needed to be made to have various shapes.

To this end, in the embodiment of the present invention, an operation direction, a shape, and the like of a knife which forms cogs on a thread are adjusted. This is automatically manufactured by controlling a multi-shaft motor according to a predetermined value after a required shape is designed and stored in a programmable logic controller (PLC).

Figure 2:
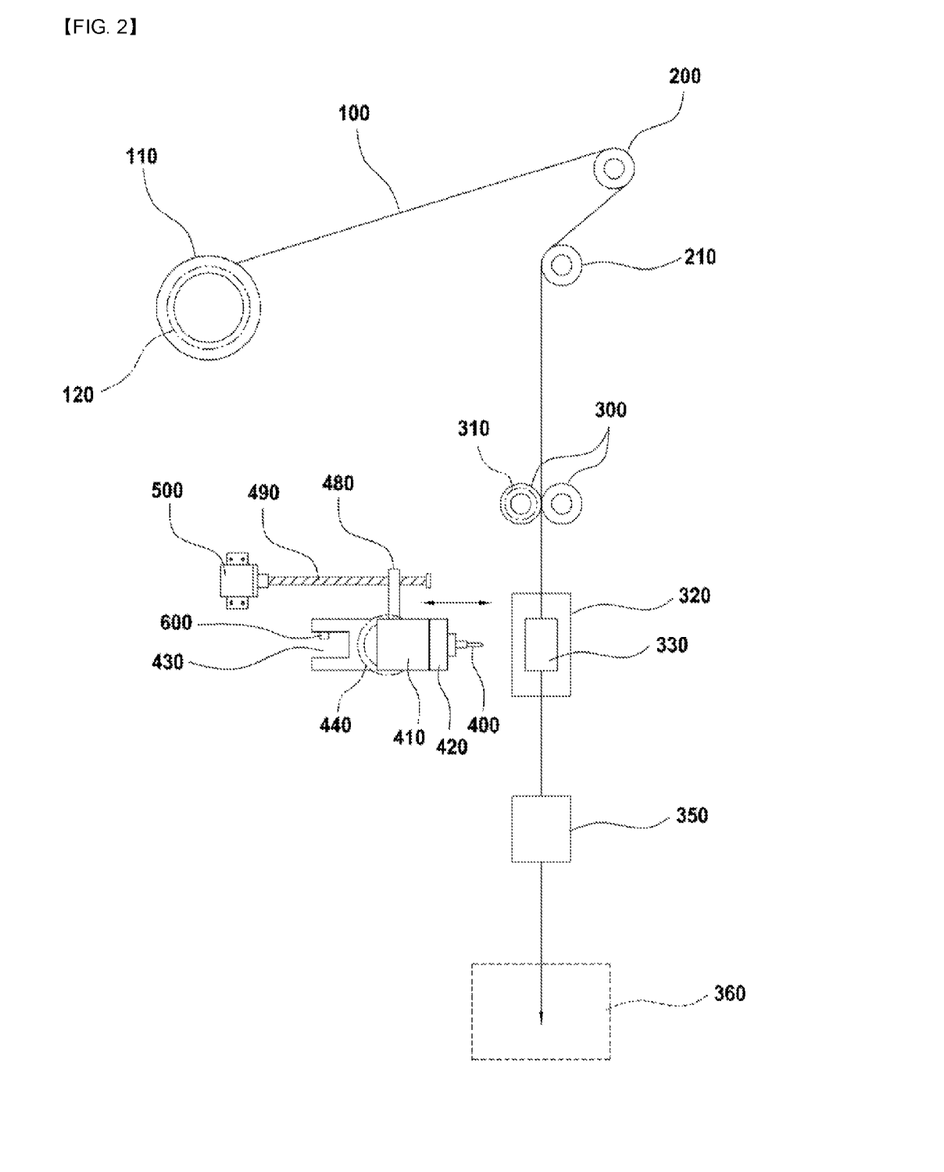
FIG. 2 is a schematic plan view illustrating a configuration of an apparatus for forming cogs on a surgical thread (suture thread) according to an embodiment of the present invention.
Figure 5:
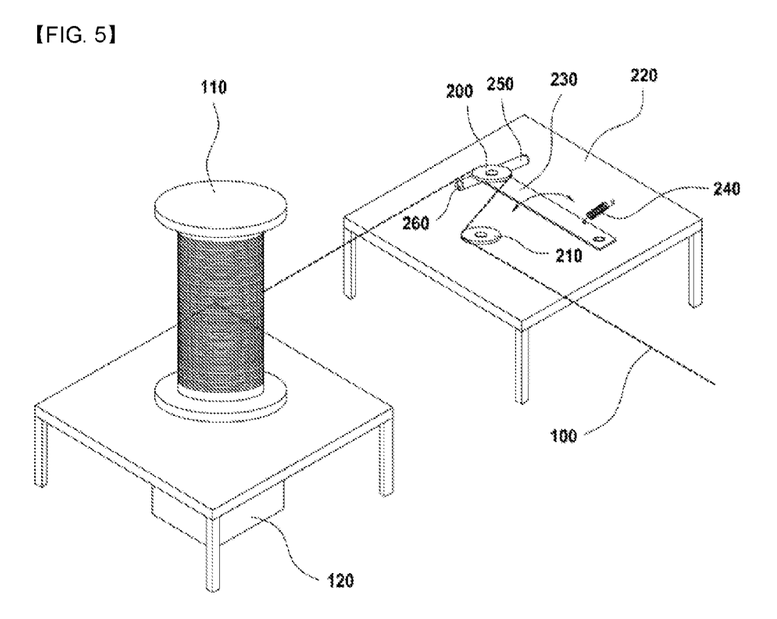
FIGS. 5 to 8 are schematic views illustrating main components included in the apparatus for forming cogs on the surgical thread (suture thread) according to the embodiment of the present invention.

More specifically, as illustrated in FIGS. 2 and 5, an apparatus for forming cogs on a surgical thread according to an embodiment of the present invention includes a bobbin 110 around which a suture thread 100 is wound.

In addition, the bobbin 110 may be rotated by a first motor 120 installed thereunder.

Here, the fixing of the first motor 120 and installation of the bobbin 110 are performed using a bobbin base 130 illustrated in FIG. 5, and since a plate-installation structure such as the bobbin base 130 is widely known, the specific description is omitted.

In addition, a first tension roll 200 is provided to be spaced apart from the bobbin 110, and as a second tension roll 210 is provided to be alternate with the first tension roll 200, the suture thread 100 passes through the first and second tension rolls 200 and 210, and thus, a constant tensile force is maintained.

Here, each of the first and second tension rolls 200 and 210 is rotatably installed on a tension roll base 220, and particularly, the first tension roll 200 is movably provided to control the tensile force.

That is, as illustrated in FIG. 5, the first tension roll 200 is rotatably and axially fixed on a top surface of one end of an operation member 230, and the other end of the operation member 230 is rotatably and axially fixed on the tension roll base 220.

In addition, one end of a tension spring 240 is fixed to a part of the operation member 230, and the other end of tension spring 240 is fixed on the tension roll base 220.

Accordingly, since the second tension roll 210 is installed at an inner side compared to the first tension roll 200, in other words, in a direction opposite a position at which the tension spring 240 is installed, even though the suture thread 100 which passes through the first tension roll 200 and the second tension roll 210 tends to pull the first tension roll 200 toward the second tension roll 210, the suture thread 100 may maintain a suitable tensile force because the tension spring 240 elastically pulls in the opposite direction.

In addition, a moving groove 250 in a long hollow shape is formed in the tension roll base 220 at a position under the first tension roll 200, and a part of a shaft of the first tension roll 200, in other words, a lowered end thereof, moves along the moving groove 250 therein while inserted in the moving groove 250.

Here, the moving groove 250 is formed in a direction in which the first and second tension rolls 200 and 210 face each other, and a limit switch 260 is installed at one end of the moving groove 250, preferably, an the end close to the second tension roll 210.

Here, the limit switch 260 outputs a signal for a driving control of the first motor 120 for driving the bobbin 110, for example, when a length of the suture thread 100 unwound from bobbin 110 is not sufficient, since a tensile force of the suture thread 100 increases, the suture thread 100 overcomes an elastic force of the tension spring 240, and pulls the first tension roll 200 toward the second tension roll 210. At this point, a roll shaft touches the limit switch 260 provided inside the moving groove 250. Then, the first motor 120 is rotated by the signal of the limit switch 260, and the suture thread 100 wound around the bobbin 110 is unwound to release an excessive tensile force, to maintain the suitable tensile force, and to continuously and smoothly provide the suture thread 100.

Meanwhile, as illustrated in FIGS. 2 to 4, and 6, the suture thread 100 which passed through the second tension roll 210 is inserted between a pair of friction rolls 300 to be pulled. More specifically, the friction roll 300 pushes the suture thread 100 in an opposite direction, and when seen from a side of the bobbin 110, the suture thread 100 is pulled. Accordingly, a tensile force applied to the suture thread 100 is initially generated by the friction roll 300.

Figure 6:
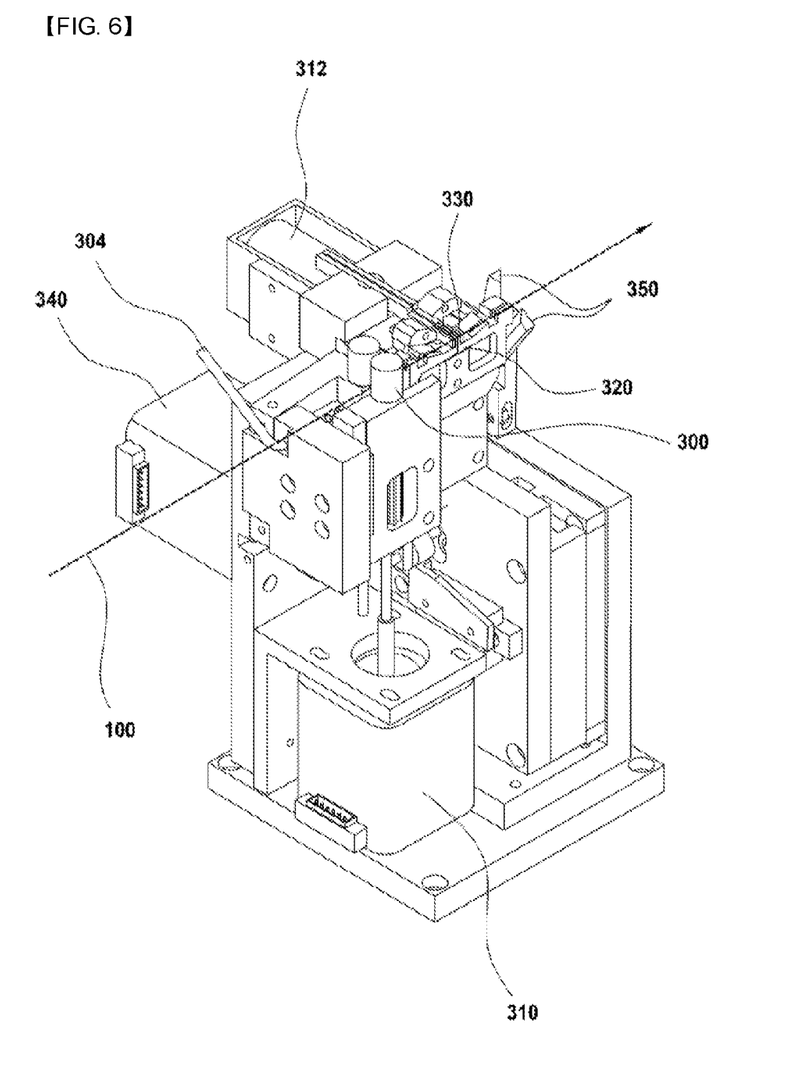

Here, it is preferable that a second motor 310 be installed under any one of the friction rolls 300 to rotate the friction roll 300 and roughness be provided on a surface of the friction roll 300 to correctly push the suture thread 100 without slipping.

It is more preferable that artificial diamond be coated on a surface of the friction roll 300.

In addition, a roller opening lever 304 which may open and close a roll fixing block 302 in which the friction roll 300 is installed using the principle of the lever may be further provided to open the friction roll 300.

In this case, although not illustrated, a pair of roll fixing blocks 302 which are elastically coupled by a spring open the friction roll 300 using the roller opening lever 304, input the suture thread 100, and control a position of the suture thread 100, and then, when the pair of roll fixing blocks 302 are released, the friction roll 300 is automatically closed by an elastic force.

In addition, a supporter 320 is provided adjacent to the friction roll 300, a push plate 330 is provided on the supporter 320, and the push plate 330 is provided to be vertically movable by a third motor 340 with a predetermined period.

Figure 4:
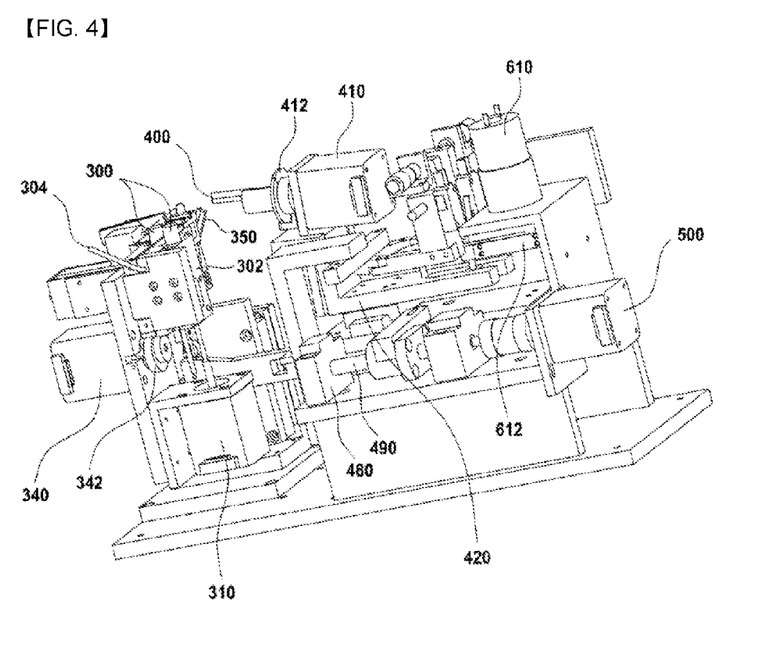

In this case, as illustrated in FIG. 4, a periodic vertical movement of the push plate 330 may be easily performed when a vertical moving cam 342 is fixed to a rotational shaft of the third motor 340 and an elastically restoring structure (using a spring) is provided to be raise and lowered the push plate 330 by the vertical moving cam 342.

In addition, the suture thread 100 passes under the push plate 330, and when the push plate 330 is lowered, the push plate 330 pushes and fixes the suture thread 100 to a top surface of the supporter 320, and when the push plate 330 is raised, since the suture thread 100 is not fixed, the suture thread 100 may be in a movable state.

Of course, the third motor 340 may not necessarily use a rotating motor and may also use a small pneumatic or hydraulic pressure cylinder as a different, easily designable method.

Furthermore, when any one of the friction rolls 300 is provided to be vertically movable, since suture threads 100 are twisted while being engaged with each other, in other words, twisted in a spiral, the cogs may be formed in even more various shapes.

In this case, a method in which any one of the friction rolls 300 rotates and vertically moves may be a method involving a cam described above and may be provided with a different, known method for an ascending and descending unit such as a cylinder to vertically move in a fine range, and also an extent of twisting the suture thread 100 may also be controlled by adjusting the movement.

In addition, as cutting scissors 350 (see FIG. 2) are installed at an end of the supporter 320, that is, a side at which the suture thread 100 moves to be discharged, a suture thread 100 on which cogs are formed is cut by a predetermined length, and the cut suture thread 100 falls to a tray 360 to be stored.

Figure 3:
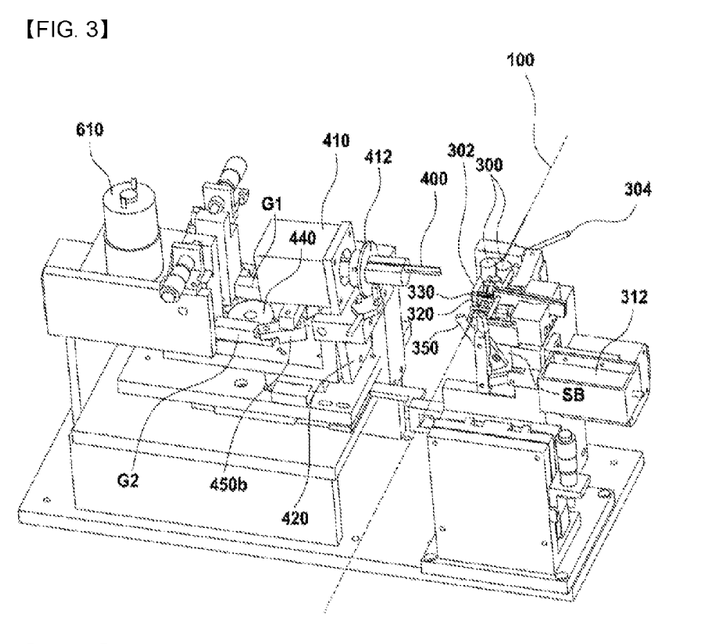
FIGS. 3 and 4 are partial perspective views illustrating an example of the apparatus for forming cogs on the surgical thread according to the embodiment of the present invention.

Here, as illustrated in FIG. 3, a blade on one side of the cutting scissors 350 is fixed to a support block SB, and a blade on the other side may be linked to a solenoid 312 to cut the suture thread 100 by a predetermined length which moves along a movement of the solenoid 312.

Figure 7:
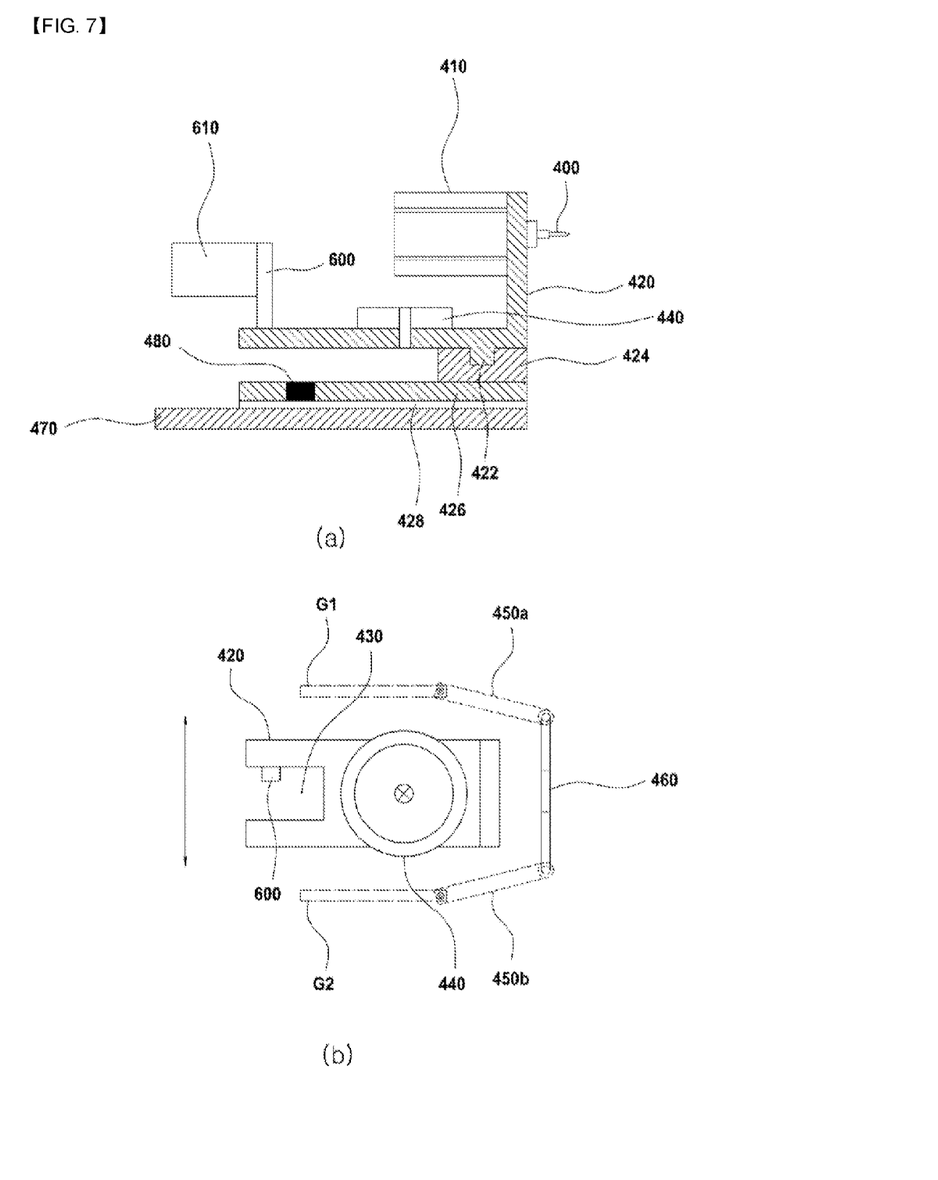
Figure 8:
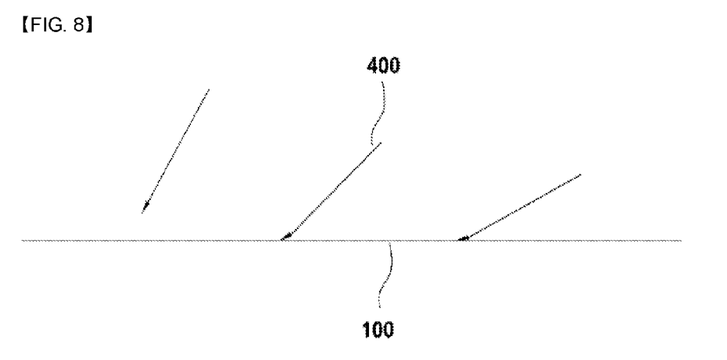

Meanwhile, as illustrated in FIGS. 2, 7A, and 7B, a cog-forming knife 400 is provided in front of the supporter 320. Here, FIG. 7A is a schematic side view and FIG. 7B is a plan view illustrating a main portion.

The cog-forming knife 400 is fixed to a sensor reference plate 412 fixed to a rotational shaft of a fourth motor 410 and rotates within a predetermined angle.

Here, since the fourth motor 410 has to perform smooth and repeated rotations within the predetermined angle, it is preferable to use a stepping motor.

In addition, the fourth motor 410 is fixed to a motor base 420, the motor base 420 is a bracket in an approximately 'L' shape, and as illustrated in FIG. 7B, an operation inducing groove 430 in a '⊏' shape cut of a predetermined depth is formed in a bent lower end surface of the motor base 420.

In addition, a rotating wheel 440 which has a diameter greater than a width of the motor base 420 is rotatably fixed on the bent lower end surface of the motor base 420, and the rotating wheel 440 is provided to be guided by a pair of first and second inclination guides 450a and 450b interposing the rotating wheel 440 and obliquely disposed from the horizontal in a forward and backward direction, that is, in a length direction of the cog-forming knife 400.

In this case, while the motor base 420 is moving left or right in a state in which the rotating wheel 440 is fixed to a top surface of a lower end of the motor base 420, the rotating wheel 440 comes into contact with any one of the facing surfaces of the first and second inclination guides 450a and 450b, move along the surface thereof such that the motor base 420 is moved in an oblique direction.

In other words, cuts can be formed when the cog-forming knife 400 moves toward a suture thread 100 and simultaneously the cog-forming knife 400 comes into contact with the suture thread 100 and moves from a length direction of the suture thread 100 to a direction of or in a direction opposite a movement of the suture thread 100 without stopping at any position.

When the cog-forming knife 400 does not move as described above, as illustrated in FIG. 1, cuts in an inclined shape is not able to be formed, and since only one position is vertically cut, a tensile force of the position becomes extremely low, and the position may be easily cut. However, in the embodiment of the present invention, cuts in an inclined shape are easily formed by a device due to automation, and this is one of the important features of the embodiment of the present invention.

In addition, as leading ends of the first and second inclination guides 450a and 450b are linked to each other by a fine adjustment method such as a micrometer 460 to simultaneously move like a turnbuckle and to adjust an angle of inclination, the angle of inclination and a depth of each cut of the cogs may be freely adjusted.

Furthermore, to operate as described above, since the motor base 420 has to move laterally as well as move in a forward and backward direction, at least two linear motor (LM) guides are provided.

That is, a laterally moving slider 422 is formed in a width direction at a part of the lower end surface of the motor base 420, the laterally moving slider 422 is assembled to a laterally moving LM guide 424, the laterally moving LM guide 424 is fixed to a top surface of a forward and backward moving slider 426, a forward and backward moving LM guide 428 is fixed in a length direction on a lower end surface of the forward and backward moving slider 426, and the forward and backward moving LM guide 428 is assembled to a top surface of a base plate 470.

Accordingly, the forward and backward moving slider 426 may move forward and backward along the forward and backward moving LM guide 428 with respect to the base plate 470, the laterally moving LM guide 424 may in the end move forward and backward at the same time since the laterally moving LM guide 424 is integrally fixed to a top surface of the forward and backward moving slider 426, the forward and backward moving slider 426 is assembled to the laterally moving LM guide 424, and thus the motor base 420 may move laterally.

Accordingly, the motor base 420 may move forward, also may move laterally, and be obliquely guided by the first and second inclination guides 450a and 450b.

In addition, a link member 480 is vertically fixed to one side surface of the forward and backward moving slider 426, a ball screw 490 is tooth-coupled to an protruding end of the link member 480 in a direction perpendicular to the link member 480, and the ball screw 490 is connected to a rotational shaft of a fifth motor 500.

Here, as illustrated in FIG. 7A, since the link member 480 is disposed under and spaced apart from the motor base 420, a position of the link member 480 is a lower space of the first and second inclination guides 450a and 450b which are disposed to guide while being in contact with the rotating wheel 440 installed on the top surface of a lower end of the motor base 420, and thus the link member 480 does not interfere with the first and second inclination guides 450a and 450b.

In addition, a lateral operation bench 600 in a rod shape is vertically arranged on the operation inducing groove 430, and a sixth motor 610 is installed at an upper end of the lateral operation bench 600 and may move the lateral operation bench 600 left, that is, toward the first inclination guides 450a, or right, that is, toward the second inclination guides 450b according to a rotational direction thereof.

In this case, the sixth motor 610 and the lateral operation bench 600 may be eccentrically fixed on a circular plate and be operated in a method involving a cam.

Accordingly, when the lateral operation bench 600 moves left, the motor base 420 also moves left along the laterally moving LM guide 424, and at this point, when the rotating wheel 440 comes into contact with the first inclination guides 450a, since the sixth motor 610 stops, the rotating wheel 440 is eventually provided to move along a contact surface of the first inclination guides 450a and vice versa.

Here, since the sixth motor 610 has to use a geared motor for a quick movement, the sixth motor 610 has an elastic force, and therefore, as illustrated in FIG. 4, may be fluidly operated when an elastic plate 612 is used.

In addition, when determining a direction of cogs, the sixth motor 610 may be provided to be automatically controlled by a setting that is set in advance in a PLC.

For example, when the rotating wheel 440 moves along the first inclination guides 450a, cogs in a shape of a lower side shown in FIG. 1B is formed, and when the rotating wheel 440 moves along the second inclination guides 450b, cogs in a shape shown in FIG. 1A is formed.

Figure 1:
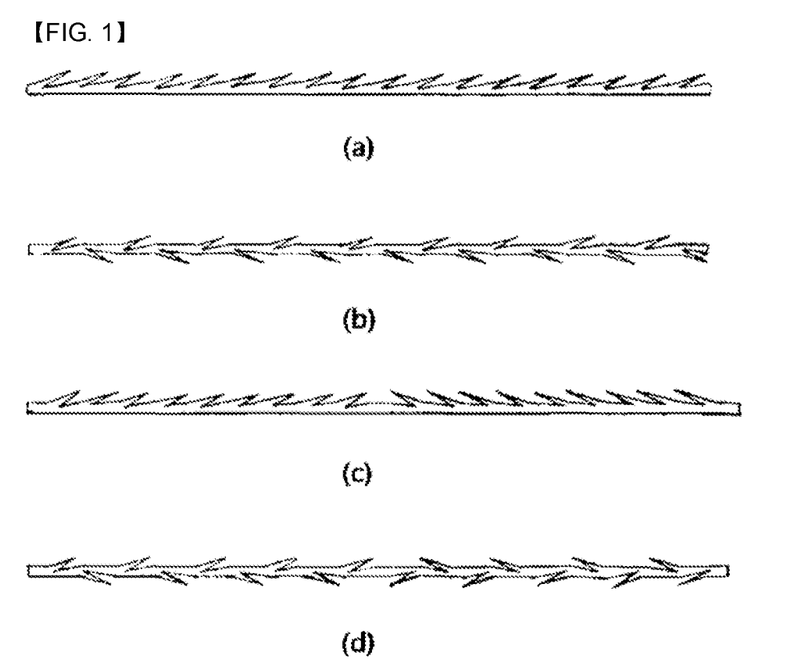
FIG. 1 shows views illustrating example suture threads on which cogs according to a conventional technology are formed.

In addition, since the cog-forming knife 400 is formed for a knife blade 402 to be raised with an inclination and the cog-forming knife 400 is chamfered, the knife blade 402 first comes into contact with a corner of an operation bench provided on the supporter 330 rather than first coming into contact with a suture thread 100. Then, since the cog-forming knife 400 simultaneously rotates and laterally moves in the above-described state, the knife blade 402 rotates as if lying in a direction of a width of the blade, moves forward, moves left or right, accordingly cuts and slightly lifts the suture thread 100 at a moment of coming into contact with the suture thread 100, and thus may correctly form cogs such as illustrated in FIG. 1.

To further describe to help understand sufficiently, although a length and a depth of cogs are determined by a movement amount of the fourth motor 410, a ratio of the length and the depth is determined by the initially set micrometer 460.

That is, although the cog-forming knife 400 is moved by the same amount by the fourth motor 410, a length of a cog, that is, a protrusion is changed by an angle of the cog-forming knife 400. In other words, the length of the cog is changed by an angle of inclination of a rotational shaft of the fourth motor 410.

Accordingly, to manufacture a thread having various thicknesses in the range of 0.1 to 0.6 mm, that is, to smoothly process a suture thread 100 without being disconnected, the cog-forming knife 400 has to be inclined and fixed in a state in which the cog-forming knife 400 always matches the center of the fourth motor 410.

In addition, when cogs are formed, sizes and depths of the left and the right thereof may be formed to be different or the same and achieved by determining a ratio of the depth and the length, and the cogs are formed from at a moment of meeting when the inclined knife blade of the cog-forming knife 400 intersects with a surface of a suture thread 100.

Accordingly, when the knife blade obliquely comes into contact with a suture thread 100 from the start, since very thin skin is formed, the cog-forming knife 400 has to be provided to form cuts in a required shape by rotating and lying the knife blade in a state in which the knife blade is suitably inserted.

To this end, as illustrated in FIG. 7B, when first and second horizontal guides G1 and G2 are further respectively linked to rear ends of the first and second inclination guides 450a and 450b to guide the rotating wheel 440, since the rotating wheel 440 straightly moves along any one of the first and second horizontal guides G1 and G2 which is disposed in contact with the rotating wheel 440 and obliquely moves along any one of the first and second inclination guides 450a and 450b from a point of an end of the first and second horizontal guides G1 and G2, the above-described problem may be solved sufficiently.

For example, when the rotating wheel 440 is adjusted to come into contact with the first horizontality guide G1 by the sixth motor 610, since the rotating wheel 440 first moves straight along the first horizontal guide G1 and obliquely moves, in other words, moves in an inclined direction along the first inclination guides 450a from an end of the first horizontality guide G1, that is, a position of linked to the first inclination guides 450a, the cog-forming knife 400 having an angle of inclination linearly moves toward a suture thread 100, simultaneously rotates, lies, obliquely moves along the first inclination guides 450a by the fourth motor 410 at the moment when coming into contact which suture thread 100. Accordingly, the suture thread 100 is formed to have cogs in an approximately 'V' or 'seagull' shape, that is, thorn shaped cogs.

Figure 10:
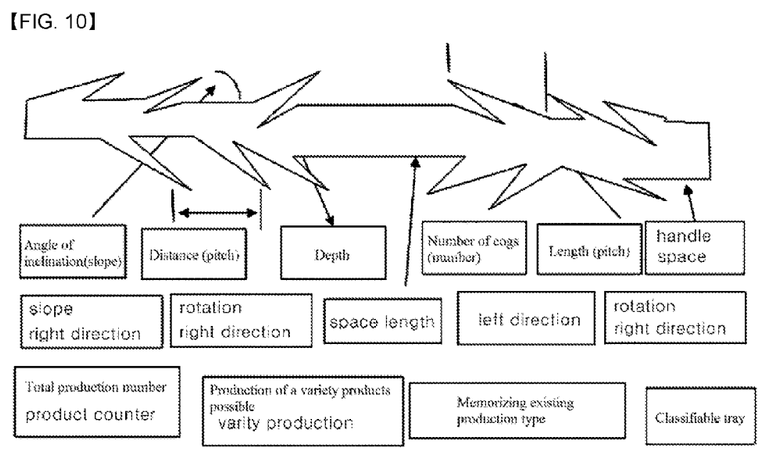
FIG. 10 is a view illustrating various examples of cogs formed on the suture thread according to the embodiment of the present invention.

Accordingly, by varying positions at which the first and second horizontality guides G1 and G2 respectively meet the first and second inclination guides 450a and 450b, depths of cuts may be changed freely as illustrated in FIG. 10, all of a shape, a direction, a depth, and a size of cogs may be formed using one apparatus according to the embodiment of the present invention, and thus the usefulness may be maximized.

In addition, relating to forming cogs, the cogs start to form from a moment when a surface of a suture thread 100 comes into contact with an inclined portion of the knife blade. With a direction of the suture thread 100 and the lying knife blade defining a plane, when the suture thread 100 is perpendicular to the knife blade, the cogs are not formed, and when an angle between the suture thread 100 and the knife blade becomes approximately 100° which is a little big, the cogs are formed according to an amount of movement.

At this point, to insert the knife blade in the suture thread 100 when the suture thread 100 comes into contact with the knife blade, an end portion of the knife blade has to be slightly inclined upward with respect to a movement direction seen from an entrance from which the suture thread 100 comes out, that is, the front thereof as well as X and Y axes. Then, when the suture thread 400 comes into contact with the knife blade, cogs formed to have a length corresponding to an angle of inclination of the fourth motor 410 by an inclination of the knife blade and a movement of a shaft of a moving motor and a depth thereof is determined according to an inclination of the knife blade.

As described above, the reason why the knife blade of the cog-forming knife 400 is obliquely disposed is to induce a smooth contact with a suture thread 100 when coming into contact with the suture thread 100 and to adjust a depth thereof since the depth also becomes deep according to the inclination.

In addition, it is preferable for the knife blade to smoothly process without mechanically colliding by providing the cog-forming knife 400 to be movable in a Z axis direction, that is, vertically movable.

As describe above, since the apparatus according to the embodiment of the present invention has too many adjustment points, the apparatus has to be provided to safely operate and not to break or destroy the knife blade or devices by controlling to apply a current between the contacting knife blade and the plate to stop the apparatus in an emergency or to avoid the collision when the knife blade collides a plate such as the supporter by a faulty adjustment.

In addition, when a suture thread departs from a path, since the suture thread does not become manufactured, it is preferable that a sensor which may check whether the suture thread 100 departs from the moving path be provided for alarming or stopping the apparatus to correct for the departure when the suture thread 100 departs from the moving path.

Furthermore, since several tens of suture threads 100 are used at once, it is preferable that an arrangement method be included which increases process efficiency by arranging the front and rear ends of the suture threads 100.

In addition, a process of a suture thread 100 is processed by data input in the PLC, and as illustrated in FIG. 10, the number of cogs, a direction of the cogs, a rotational direction of the suture thread, a pitch of the cogs, a depth of the cogs, a length of the cogs, a curved degree of cut cross-section of the knife blade, an inserting angle of the knife blade, a length where no processing, a cut position, whether various kinds are manufactured at one time or one by one, whether various kinds are manufactured at one time or the total is produced, how many products are produced, and the like may be input and defined in advance using such data. The apparatus is very suitable for an automatic production and various kinds of cogs may be formed using one apparatus.

The above-described apparatus according to the embodiment of the present invention forms cogs through the following method.

Figure 9:
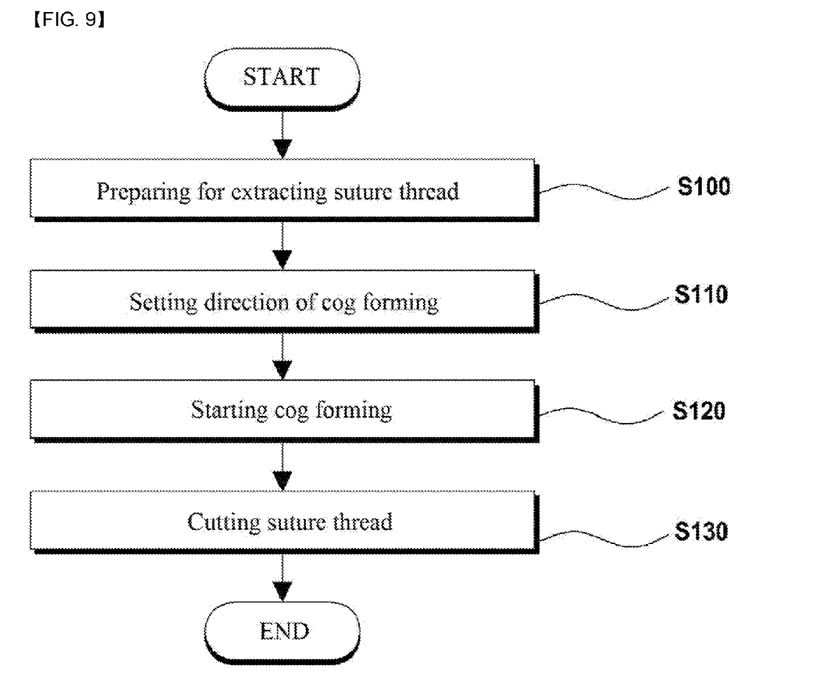
FIG. 9 is a flowchart for describing a method of forming cogs on the surgical thread according to the embodiment of the present invention.

That is, as illustrated in FIG. 9, preparing for extracting a suture thread S100 is performed first.

The preparing for extracting the suture thread S100 is a process to maintain a state capable of extracting the suture thread, and the extracting of the suture thread is performed by rotating the second motor 310 as previously described and pushing the suture thread 100 engaged with the friction roll 300 toward an output side.

Then, the suture thread 100 wound around the bobbin 110 is unwound and withdrawn while being maintained with a suitable tensile force by a plurality of tension rolls.

When the suture thread 100 is maintained in a state capable of extracting the suture thread 100 by the above process, setting a direction of cog forming S110 is performed.

The setting of the direction of cog forming S110 is a process to determine and set whether cogs which will be formed on the suture thread 100 is formed in a length direction of the suture thread 100 or in a direction opposite the length direction. For example, forming cogs is easily controlled by counting the number of the formed cogs and moving the motor base 420 to change a direction when the number becomes greater than a preset number.

Then, when the setting of the direction of cog forming is completed, starting cog forming S120 which is a process of forming cuts in a preset direction on a surface of the suture thread 100 by extracting the suture thread 100, controlling each of the first, second, third, fourth, fifth, and sixth motors 120, 310, 340, 410, 500, and 610 at the same time, and simultaneously moving, rotating, and obliquely moving the cog-forming knife 400 are performed.

At this point, operations of gripping the suture thread 100 not to move the suture thread 100 by lowering the push plate 330 according to a movement of the cog-forming knife 400 are automatically performed according to a preset sequence.

After that, when a predetermined length or the predetermined number of the cogs are formed, cutting a suture thread S130 which cuts the suture thread 100 by a predetermined length using the cutting scissors 350 is performed.

As described above, the apparatus for forming cogs on a surgical thread and the method thereof according to the embodiment of the present invention can improve productivity, contribute to a quality improvement, enable mass production, and save production cost by completely improving a conventional method in which a worker manually formed cogs one by one to a method of automatically forming cogs through a device.

[Description of Symbols]

| | |
|---|---|
| 100: suture thread | 110: bobbin |
| 120: first motor | 200: first tension roll |
| 210: second tension roll | 300: friction roll |
| 310: second motor | 340: third motor |
| 400: cog-forming knife | 410: fourth motor |
| 500: fifth motor | 610: sixth motor |

The invention claimed is:

1. An apparatus for forming cogs on a surgical thread, comprising:
   a bobbin (110) around which a suture thread (100) is wound;
   a first tension roll (200) and a second tension roll (210) which maintain the suture thread (100) unwound from the bobbin (110) at a constant tensile force;
   a pair of friction rolls (300) through which the suture thread (100) passes to be discharged toward an output side by being pulled;
   a push plate (330) which temporally fixes the suture thread (100) moved toward the output side by the friction rolls (300) and moves upward and downward; and
   a cog-forming knife (400) which simultaneously rotates and moves forward toward the suture thread (100) fixed by the push plate (330), obliquely moves to the left or right, and forms a cut in an inclined shape on a surface of the suture thread (100) to form a cog.

2. The apparatus of claim 1, wherein roughness is provided on surfaces of the pair of friction rolls (300).

3. The apparatus of claim 1, wherein any one of the pair of friction rolls (300) is provided to vertically move to twist and move the suture thread (100).

4. The apparatus of claim 1, wherein a gap between the pair of friction rolls (300) is widened by a roller opening lever (304) operated by the principle of a lever.

5. The apparatus of claim 1, wherein:
   the cog-forming knife (400) is fixed to a rotational shaft of a motor (410) so that an angle is adjustable;
   the motor (410) is fixed to a motor base (420) in an 'L' shape;
   a rotating wheel (440) having a diameter greater than a width of the motor base (420) is fixed on a bent lower end surface thereof;
   the rotating wheel (440) is disposed to come into contact with any one of a pair of first and second inclination guides (450a and 450b) which are obliquely arranged so that the rotating wheel (440) is interposed therebetween;
   the motor base (420) is provided to be movable in X and Y directions by a plurality of sliders (422 and 426) and linear motors (LM) (424 and 428); and
   the motor base (420) is connected to a ball screw (490) rotated by a motor (500) and is provided movably.

6. The apparatus of claim 5, wherein leading ends of the first and second inclination guides (450a and 450b) are linked to each other by a micrometer (460) which is a fine adjustment unit and adjust an inclination and a depth of a cut forming a cog by adjusting an inclination of the first and second inclination guides (450a and 450b).

7. The apparatus of claim 5, wherein first and second horizontal guides (G1 and G2) in a straight-line shape are further linked to respective ends of the first and second inclination guides (450a and 450b).

8. The apparatus of claim 7, wherein the rotating wheel (440) which comes into contact with any one of the first and second inclination guides (450a and 450b) is adjusted by laterally moving the motor base (420) using a lateral operation bench (600) in a rod shape which is straightly moved in a lateral direction by a motor (610).

9. The apparatus of claim 1, wherein cutting scissors (350) are further provided at a side of an output side, at which the suture thread (100) is discharged after a cog is formed on the suture thread (100), to cut the suture thread (100) by a predetermined length.

10. The apparatus of claim 9, wherein the cutting scissors (350) cut the suture thread (100), which is moved by a solenoid (312), by the predetermined length.

11. The apparatus of claim 1, wherein the cog-forming knife (400) and a supporter (320) provided with the push plate (330) are electrically connected to perform an emergency stopping of the operation when coming in contact with each other due to a faulty operation so that the apparatus is protected.

12. The apparatus of claim 1, wherein:
   the apparatus is controlled by a programmable logic controller (PLC);
   data which is input in the PLC and variably processible includes the number of cogs, a direction of the cog, a rotational direction of the suture thread, a pitch of the cogs, a depth of the cog, a length of the cog, a curved degree of cut cross-section of the knife blade, an inserting angle of the knife blade, a length of a region with no processing, and a cut position; and
   whether various kinds are manufactured at one time, whether production is performed for all of the various kinds, and how many products are produced are input and defined in advance.

13. A method of forming a cog on a surgical thread using the apparatus for forming cogs on a surgical thread of claim 1, the method comprising:
   preparing for extracting a suture thread (S100) so that the suture thread (100) wound around the bobbin (110) passes between the first and second tension rolls (200 and 210) and the friction rolls (300) and is disposed toward the output side to extract the suture thread (100);
   setting a direction of cog forming (S110) that determines and sets whether a cog to be formed on the suture thread (100) is formed in a length direction of the suture thread (100) or in a direction opposite the length direction when the suture thread (100) is maintained in an extractable state;
   starting cog forming (S120) that simultaneously extracts the suture thread (100), moves and rotates a cog-forming knife (400), and moves the cog-forming knife (400) in an inclined direction to form a cut in a predetermined direction on the surface of the suture thread (100) when the setting of the direction of the cog forming is completed; and cutting a suture thread (S130) which cuts the suture thread (100) by a predetermined length using the cutting scissors (350) when a predetermined length or the set number of cogs are formed.

\* \* \* \* \*